United States Patent
Palestrant

[19]

[11] Patent Number: 5,827,243
[45] Date of Patent: Oct. 27, 1998

[54] COLLAPSIBLE ASPIRATION CATHETER

[76] Inventor: Aubrey M. Palestrant, 6800 N. 47th St., Paradise Valley, Ariz. 85253

[21] Appl. No.: 770,372
[22] Filed: Nov. 29, 1996
[51] Int. Cl.⁶ .................................................. A61M 25/00
[52] U.S. Cl. .......................... 604/282; 604/43; 604/280
[58] Field of Search .................................. 604/43, 93, 96, 604/158, 160, 164, 167, 169, 170, 244, 245, 247, 256, 257, 266, 264, 280, 282

[56] References Cited

U.S. PATENT DOCUMENTS

| Re. 31,873 | 4/1985 | Howes | 128/674 |
|---|---|---|---|
| 1,596,754 | 8/1926 | Moschelle . | |
| 4,134,402 | 1/1979 | Mahurkar | 128/214 R |
| 4,257,422 | 3/1981 | Duncan | 128/350 R |
| 4,317,452 | 3/1982 | Russo et al. | 128/350 R |
| 4,406,656 | 9/1983 | Hattler et al. | 604/280 |
| 4,451,252 | 5/1984 | Martin | 604/43 |
| 4,543,087 | 9/1985 | Sommercorn et al. | 604/43 |
| 4,601,713 | 7/1986 | Fugua | 604/280 |
| 4,643,711 | 2/1987 | Bates | 604/43 |
| 4,681,570 | 7/1987 | Dalton | 604/282 |
| 4,808,155 | 2/1989 | Mahurkar | 604/43 |
| 4,846,791 | 7/1989 | Hattler et al. | 604/43 |
| 5,106,368 | 4/1992 | Uldall et al. | 604/43 |
| 5,176,659 | 1/1993 | Mancini | 604/280 |
| 5,221,255 | 6/1993 | Mahurkar et al. | 604/43 |
| 5,464,398 | 11/1995 | Haindl | 604/280 |
| 5,472,418 | 12/1995 | Palestrant | 604/43 |
| 5,486,159 | 1/1996 | Mahurkas | 604/4 |
| 5,569,182 | 10/1996 | Twardowski et al. | 604/43 |
| 5,618,267 | 4/1997 | Paleshant | 604/53 |

Primary Examiner—Corrine M. Mcdermott
Assistant Examiner—Cris L. Rodriguez
Attorney, Agent, or Firm—Cahill, Sutton & Thomas, P.L.C.

[57] ABSTRACT

A partially collapsible catheter is formed as a substantially-flattened tube of flexible, collapsible plastic; a spacing member disposed within such tube allows the tube to substantially flatten and collapse in the absence of infusion fluid, but maintains at least one channel open within the tube for allowing fluid to be aspirated therethrough. During infusion, infusion fluid expands the catheter to a generally rounded configuration. The spacing member can be incorporated within a single lumen catheter; alternatively, the spacing member can divide the tube into first and second lumens for providing a dual lumen catheter.

25 Claims, 2 Drawing Sheets

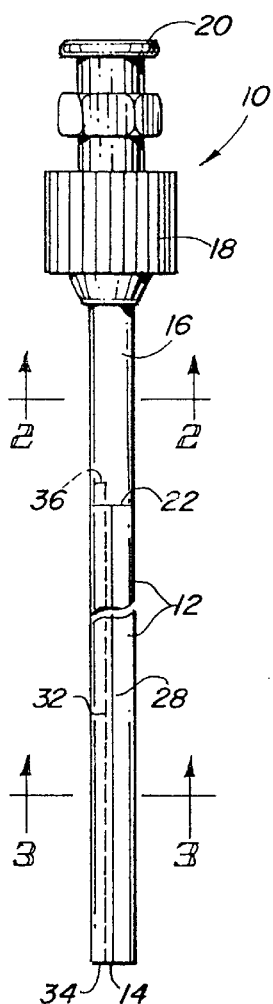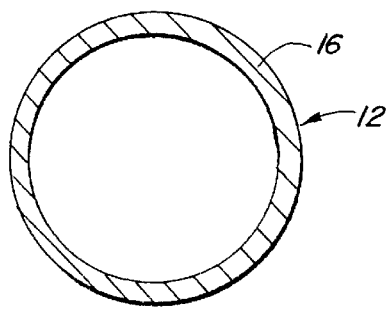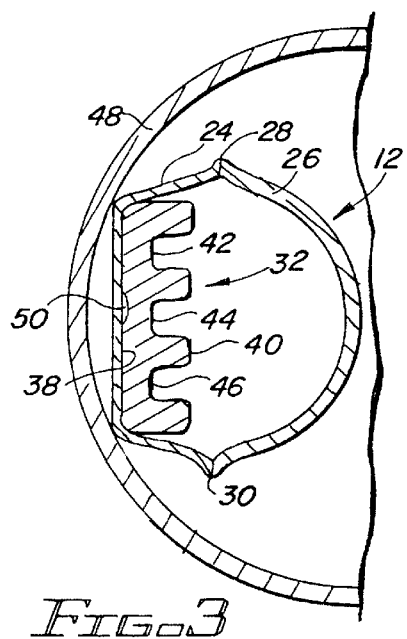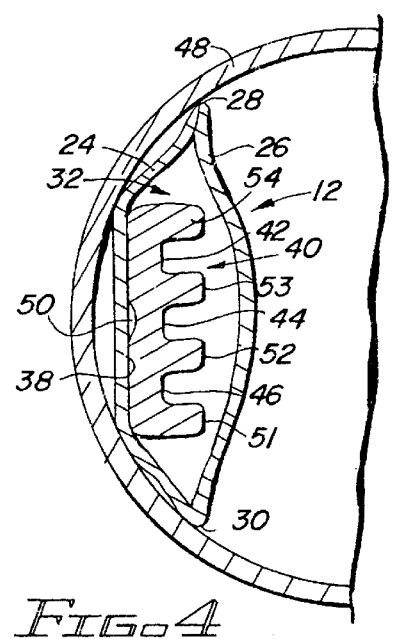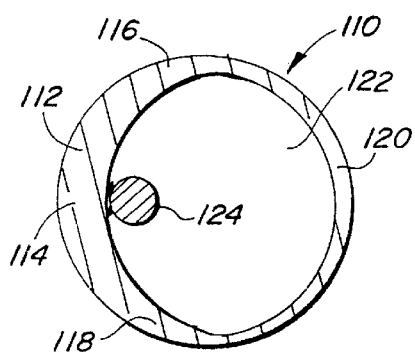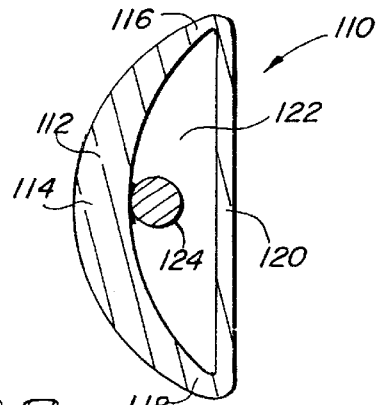

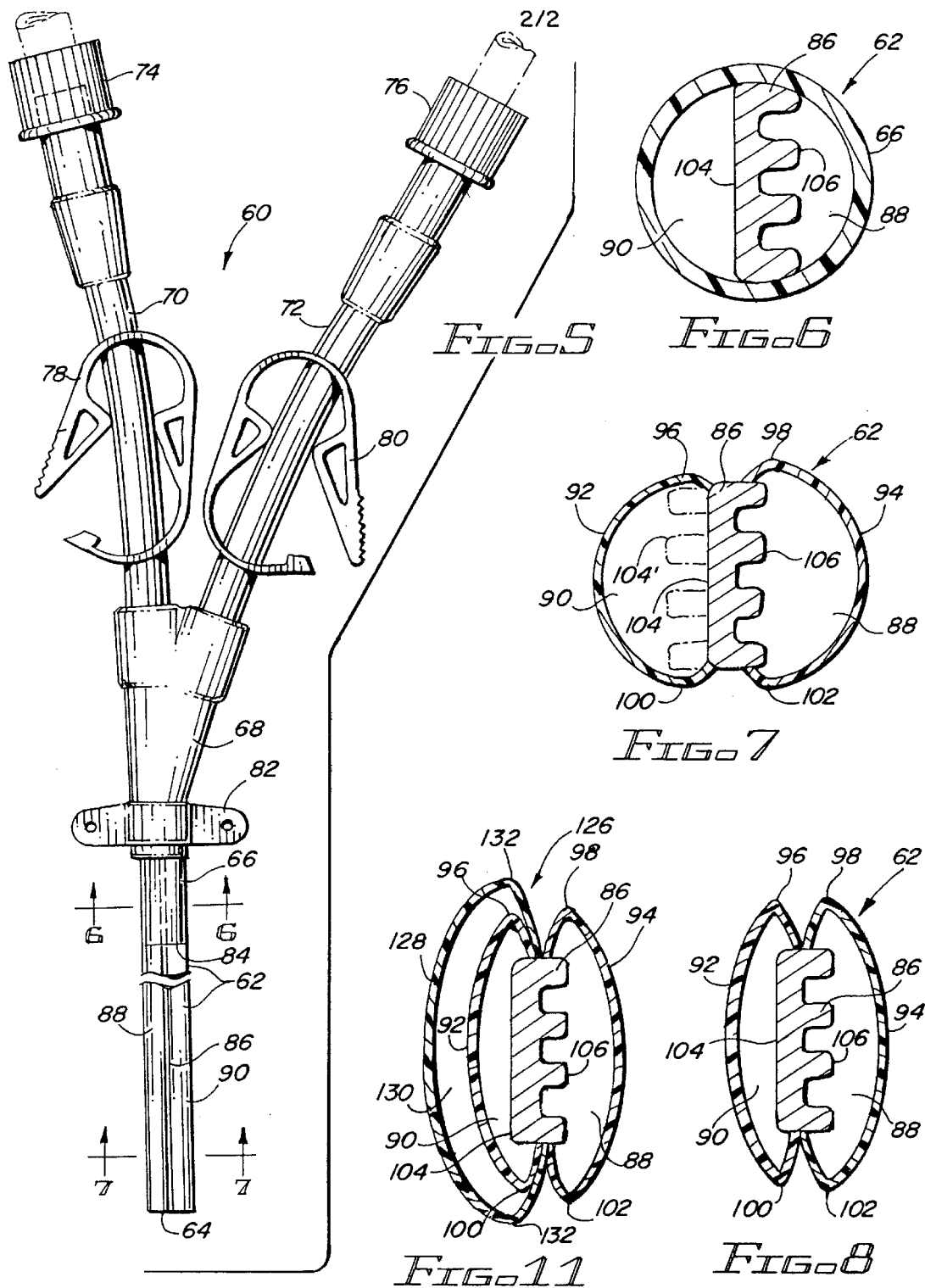

COLLAPSIBLE ASPIRATION CATHETER

BACKGROUND OF THE INVENTION

1. Field of the Invention

The present invention relates generally to catheters inserted into a patient's body for extended periods of time in order to aspirate and/or infuse fluids, and more particularly, to a substantially collapsible catheter including a passage which remains open under negative pressure.

2. Description of the Related Art

Insertion of catheters into humans and animals is a commonly performed procedure. These catheters function as a conduit for infusion of fluids or drugs, and may also be used to aspirate fluids from the body. A catheter is a foreign body, and when a catheter must remain within a patient for more than a brief period, complications may arise. Catheters are typically made from a relatively rigid plastic material with a standard, round cross-section, both to facilitate placement of the catheter into the body and to prevent one or more passages, or lumens, within the catheter from buckling or collapsing. Generally speaking, known catheters are constructed in such a way that the lumen or lumens extending therethrough retain their cross-sectional configuration unless an external mechanical force compresses the catheter.

Within Applicant's related U.S. Pat. No. 5,472,418, issued on Dec. 5, 1995, a flattened collapsible vascular catheter is disclosed for creating a collapsible infusion conduit within a blood vessel. The catheter disclosed within such patent allows an infusion lumen to collapse and flatten against the blood vessel wall when no fluid is being infused, thereby minimizing the cross-section, and exposed surface area of such catheter. However, when fluid is being aspirated from the body, a negative pressure, or suction, must be applied to the proximal end of the catheter. The application of such negative pressure will tend to seal and collapse the internal walls of the catheter unless the walls of the catheter are sufficiently rigid to resist such negative pressures. On the other hand, catheters having rigid walls tend to cause complications noted below.

It is common to place a central line catheter in one of the major veins at the top of the chest leading to the heart, such as the subclavian vein or one of the major veins of the mediastinum. However, this procedure is often accompanied by the formation of clots on the wall of the catheter. Blood clots form for several reasons. The presence of any object occupying space within a blood vessel causes turbulence and slowing of the blood flow through the vessel, and these factors induce the formation of clots. Generally, the greater the cross-sectional area of the catheter relative to the blood vessel, the greater the induced turbulence and slowing of the blood. In addition, the catheter is a foreign body, and the surface of the catheter in contact with blood acts as a nidus for clot formation. Once again, the greater the amount of surface area of the catheter or other foreign body in contact with the blood, the more likely that clots will form.

Such clots can break away and flow in the blood stream to the heart and lungs, causing severe complications. Furthermore, the formation of clots can often cause such veins to become irreversibly damaged and thrombose, preventing further blood flow through such veins. This may ultimately cause debilitating swelling of the limb being drained by these veins.

Apart from the risks of forming clots within the blood vessel, present central line catheters also suffer from susceptibility to clotting within the catheter itself. In this regard, blood enters the lumen of the catheter and forms a clot within the lumen, obstructing the passage of fluids through the catheter into the vein, and thereby rendering it unusable. While such clots may not be life threatening to the patient, blockage of the catheter can require removal and replacement of the catheter, a procedure which poses an inconvenience to both the patient and the attending physician, and adds to the cost of maintaining venous access.

U.S. Pat. No. 5,176,659 issued to Mancini discloses an expandable intravenous catheter which has a lesser diameter during insertion into a vein, and which is thereafter expanded following placement to a larger diameter. While such device simplifies insertion of the catheter, it still maintains a sizable obstruction within the vein with a significant exposed surface area, and it still permits blood to enter the lumen of the catheter in the absence of fluid flow.

U.S. Pat. No. 5,106,368 to Uldall et al. discloses a dual lumen catheter for vascular access. The distal portion of the catheter includes two tubular members attached to each other, only one of which is collapsible. The catheter is inserted into a blood vessel through a peel-away sheath, and over both a stiffening cannula and a guide wire. The collapsible lumen returns to its original circular shape once placed in the blood vessel. Thus, no reduction of the cross-sectional area, or surface area, of the catheter is achieved after the catheter is placed. In addition, blood can still enter both lumens of the catheter in the absence of fluid flow.

U.S. Pat. No. 4,406,656 issued to Hattler et al. discloses a multi-lumen catheter adapted to be inserted through the center of an insertion needle into the vein of a patient. The catheter disclosed by Hattler et al. includes two or more collapsible lumens formed around a flexible, but non-collapsible, central lumen. The collapsible lumens expand outwardly under the pressure of fluid flow and collapse to a smaller cross-sectional area in the absence of fluid flow. However, the central lumen of the Hattler et al. device is formed of materials which retain the shape of the central passageway whether or not fluids flow therethrough. Thus, even when the collapsible lumens are collapsed, the device disclosed by Hattler et al. still approximates the cross-sectional area of a conventional single lumen catheter. Indeed, Hattler et al. state that the central lumen of the disclosed multi-lumen catheter requires a certain degree of stiffness or rigidity to provide sufficient structural support so that the catheter can be handled as are conventional catheters. While the device disclosed by Hattler et al. somewhat reduces the cross-sectional area of a multi-lumen catheter, it does not reduce the cross-sectional area or surface area of the catheter below that of a conventional single lumen catheter, nor does it prevent blood from entering the central, non-collapsible lumen in the absence of fluid flow. In addition, none of the collapsible lumens described by Hattler et al. may be used for aspirating fluids, since the application of negative pressure to such lumens effectively seals off such lumens.

Accordingly, it is an object of the present invention to provide a catheter which is substantially collapsible when not being used to infuse fluids, in order to present a minimal cross sectional area and surface area, while still being capable of aspirating fluids from the body.

It is another object of the present invention to provide such a catheter which is sufficiently resilient to expand during infusion to provide a significant fluid flow path into the body during infusion.

A further object of the present invention is to provide such a catheter which, when placed in the vascular system, reduces the likelihood of the formation of clots within a blood vessel into which the catheter is placed.

It is another object of the present invention to provide such a catheter which, when placed in the vascular system, presents a minimal cross-section obstruction to the normal flow of blood within the blood vessel when the catheter is not being used for infusion, while providing a satisfactory flow path to infused fluids during infusion procedures.

It is still another object of the present invention to provide such a catheter which, when placed in the vascular system, minimizes the surface area of the catheter exposed to the blood when infusion procedures are not being performed.

It is a further object of the present invention to provide such a catheter which, when placed in the vascular system, reduces the likelihood of blood forming a blockage within the lumen of the catheter.

These and other objects of the present invention will become more apparent to those skilled in the art as the description of the present invention proceeds.

SUMMARY OF THE INVENTION

Briefly described, and in accordance with a preferred embodiment thereof, the present invention is a substantially collapsible catheter tube having leading and trailing ends and formed in part by a reinforcing wall that extends between the leading and trailing ends of the catheter tube. This reinforcing wall is flexible, but resists collapse along the longitudinal axis of the catheter tube. The reinforcing wall includes opposing first and second side edges. The catheter tube also includes a flexible strip of material extending between the leading and trailing ends of the catheter tube. A first edge of the flexible strip is joined to the first side edge of the reinforcing wall, and the second opposing edge of the flexible strip is joined to the second side edge of the reinforcing wall. In this manner, a fluid-conducting lumen is formed between the reinforcing wall and the flexible strip. Unlike the reinforcing wall, the flexible strip is collapsible and does not resist lateral deformation. The trailing end of the catheter tube is adapted to receive fluid to be infused into a patient's body, and also to convey fluid aspirated from the patient's body. The leading end of the catheter tube provides a port within the patient's body through which infused fluid is introduced into the patient's body, and through which aspirated fluid can be removed from the patient's body. The flexible strip expands away from the reinforcing wall to a generally rounded shape when fluid is infused through the catheter tube into the patient. When infusion is not being performed, the flexible strip can deform toward the reinforcing wall to a more flattened configuration. However, the catheter tube includes a spacing mechanism for preventing the flexible strip from entirely sealing the lumen when fluid is being aspirated therethrough.

In one preferred embodiment of the present invention, the aforementioned reinforcing wall has, in cross-section, a generally crescent-shaped configuration. This reinforcing wall includes a relatively thick middle region resistant to deformation, tapering outwardly toward a pair of relatively thin end regions that are not as resistant to deformation. The flexible strip of material extends across the bowed end regions of the reinforcing wall along its length and is joined thereto to form the fluid-conducting lumen in conjunction with the reinforcing wall. The reinforcing wall is bowed outwardly to bias the end regions thereof apart from one another, thereby stretching the flexible strip into a flattened configuration when no fluid is being infused through the catheter tube. However, when fluid is infused through the catheter tube, the flexible strip expands outwardly to a generally rounded shape, further arching and rounding the reinforcing wall, as well. Aspiration without collapse of the lumen is permitted either by the outward bowing of the reinforcing wall, in which case the outwardly bowed ends of the reinforcing wall themselves serve as a spacing mechanism, or by adding a spacing member, such as one or more ribs, to the interior of the reinforcing wall.

Another aspect of the present invention relates to a substantially collapsible catheter apparatus for providing a passage into a patient's body to infuse fluids therein and/or to aspirate fluids therefrom, and including first and second elongated, generally flattened strips of material that are flexible and collapsible; each such strip of flexible material extends between leading and trailing opposing ends, and each having first and second opposing edges. The first edge of the second strip is joined with the first edge of the first strip, and the second edge of the first strip is joined with the second edge of the second strip to form an elongated, flattened tube having opposing leading and trailing ends. In addition, an elongated spacing member is disposed within the elongated tube formed by the first and second strips of flexible material and includes at least one open channel extending therealong to provide a reinforced aspiration channel.

The leading end of the aforementioned spacing member extends proximate the leading ends of the first and second strips of flexible material, and the opposing trailing end of the spacing member extends proximate the trailing ends of the first and second strips of flexible material. The spacing member is secured to the first strip of flexible material but is not secured to the second strip of flexible material. The channel or channels formed in the spacing member face the second strip of flexible material.

The trailing end of the elongated tube is adapted to either receive fluid to be infused into the patient's body, or to convey fluid aspirated from the patient's body. On the other hand, the leading end of the elongated tube provides a port through which infused fluid received at the trailing end of said tube can be introduced into a patient's body, and through which fluid within the patient's body can be aspirated.

During infusion of fluid through the elongated tube, the second strip of flexible material expands away from the channels of the spacing member, and the tube assumes a generally rounded shape. When the infusion procedure is terminated, the first and second strips of flexible material collapse toward one another into a substantially flattened configuration containing the spacing member therein, and thereby assume a more compact shape.

When it is desired to aspirate fluid from the patient, negative pressure is applied to the trailing end of the elongated tube. Such negative pressure tends to further collapse the first and second strips of flexible material toward one another; however, the spacing member channels preclude a total collapse of the elongated tube and maintain open channels along the elongated tube through which fluid can be aspirated from the patient's body.

According to a further aspect of the present invention, a dual lumen catheter is provided that is substantially collapsible and which can infuse fluids into a patient's body and also aspirate fluids from the patient's body. First and second elongated, and generally flattened, strips of flexible material, each having leading and trailing opposing ends and first and second opposing edges, are joined along their respective first and second edges to form an elongated tube having opposing leading and trailing ends. An elongated spacing member is disposed within such elongated tube extending between the first and second ends thereof. A first side edge of the spacing member is joined with the first edges of the first and second strips of flexible material, and a second side edge of the spacing member is joined with the second edges of the first and second strips of flexible material. Accordingly, the spacing member divides the elongated tube into first and second lumens bounded by the first and second strips of flexible material, respectively.

First and second connector tubes are coupled, as by a connector hub, to the first and second lumens at the trailing ends of the elongated tube. These first and second connector tubes are adapted to receive fluid to be infused into, and to convey fluid aspirated from, a patient's body. The leading end of the elongated tube extends within the patient's body following placement of the catheter, and provide two ports through which infused fluid received at the trailing end of the elongated tube can be introduced into the patient's body, and provide at least one port through which fluid can be aspirated from a patient's body.

In the preferred form of the dual lumen catheter described above, the spacing member includes at least one open channel extending therealong and facing the first strip of flexible material within the first lumen. This spacing member allows the first and second strips of flexible material to collapse toward the spacing member and toward one another into a substantially flattened configuration in the absence of infusion fluid.

During infusion procedures, and assuming that fluid is infused through both the first and second lumens, the elongated tube expands to a generally rounded shape, only to collapse back to a substantially flattened configuration when infusion is terminated. If fluid must be aspirated, a negative pressure can be applied to the connector tube coupled with the first lumen. The spacing member maintains a channel within the first lumen to aspirate fluid from the patient's body, as needed. If desired, a similar channel, or channels, can be formed within the spacing member within the second lumen in order to aspirate through the second lumen.

In the preferred embodiment of the present invention, the aforementioned strips of flexible material are formed of a pliable, but inelastic, plastic material. Such plastic material is preferably selected from the group of plastics consisting of polyethylene, polyethylene teraphthalate, and polyvinyl chloride. Preferably, the catheter includes a non-collapsible trailing end for extending through the patient's skin and other surrounding tissues for reinforcing the catheter at the puncture site and for connection to a connector hub. If desired, a radiopaque material can extend along the elongated tube and/or spacing member for allowing the position of the tube to be viewed within the patient's body by X-rays, fluoroscope, or the like.

BRIEF DESCRIPTION OF THE DRAWINGS

FIG. 1 is a top view of a single-lumen, partially collapsible catheter constructed in accordance with the teachings of the present invention.

FIG. 2 is a cross-sectional drawing of the catheter shown in FIG. 1 taken through the plane designated by lines 2—2 in FIG. 1.

FIG. 3 is a cross-sectional drawing of the catheter shown in FIG. 1 taken through the plane designated by lines 3—3 in FIG. 1, and illustrating the placement of the catheter within a blood vessel during an infusion procedure.

FIG. 4 is a cross-sectional view of the catheter shown in FIG. 3 in its flattened configuration after the infusion procedure is terminated.

FIG. 5 is a top view of a dual lumen catheter constructed in accordance with the teachings of the present invention.

FIG. 6 is a cross-sectional view of the catheter shown in FIG. 5 taken through the plane designated by the lines 6—6 in FIG. 5.

FIG. 7 is a cross-sectional view of the catheter shown in FIG. 5 taken through the plane designated by lines 7—7 in FIG. 5 and illustrating the expanded configuration of the lumens during an infusion procedure.

FIG. 8 is a cross-sectional view of the catheter shown in FIG. 5 similar to the cross-sectional view of FIG. 7, but showing the lumens in their collapsed state following termination of the infusion procedure.

FIG. 9 is a cross-sectional view of an alternate embodiment of the present invention wherein a semi-collapsible single-lumen catheter is shown in its expanded state during a fluid infusion procedure.

FIG. 10 is a cross-sectional view of the single-lumen catheter shown in FIG. 9 in its collapsed state following termination of the fluid infusion procedure.

FIG. 11 is a cross-sectional drawing similar to that of FIG. 8 but showing a construction of triple-lumen catheter.

DETAILED DESCRIPTION OF THE PREFERRED EMBODIMENTS

Within FIG. 1, a substantially collapsible catheter is designated generally by reference numeral 10. Catheter 10 is designed to provide a passage into a patient's body to infuse fluids therein and/or to aspirate fluids therefrom. Catheter 10 includes an elongated tube 12 having a leading end 14 and an opposing trailing end 16. Leading end 14 serves as a port within the body, following placement of catheter 10, through which infused fluid introduced at trailing end 16 can be delivered into a patient's body; likewise, leading end 14 can also serve as a port within the body through which blood or other fluids can be withdrawn from the patient's body via trailing end 16.

As shown in FIG. 1, trailing end 16 of tube 12 is preferably coupled to a knurled hub connector 18 which can be manipulated by medical personnel. The upper end 20 of catheter 12 includes a female luer lock connector fitting in order to sealingly engage a male luer lock connector fitting (not shown) of an infusion line, aspiration line, etc.

As shown in FIG. 2, the trailing end 16 of catheter tube 12 has a substantially circular cross-section and is of substantial thickness for allowing tube 12 to maintain its circular shape even when trailing end 16 extends through a puncture tract formed in skin, blood vessel walls, or other tissues of the patient's body. While trailing end 16 of catheter tube 12 is flexible, it is still sufficiently rigid to avoid collapse or buckling along the puncture tract, and to prevent damage to tube 12 arising from long term manipulation of catheter 10 following placement. As shown in FIG. 1, trailing end 16 extends from hub connector 18 to a transition point designated by reference numeral 22.

On the other hand, the portion of catheter tube 12 which extends from leading end 14 to transition point 22 is intended to be partially collapsible in order to minimize the cross-sectional area occupied by tube 12 within the patient's body. Referring to FIGS. 3 and 4, the portion of catheter tube 12 extending between leading end 14 and transition point 22 includes a first elongated, generally flattened strip 24 of a flexible material, as well as a second elongated, generally flattened strip 26 of flexible material. These first and second flexible strips 24 and 26 each have a leading end adjacent leading end 14 of tube 12, as well as opposing trailing ends adjacent transition point 22. A first edge of strip 24 and a first edge of strip 26 are joined to each other along a first seam, or pleat, 28. Likewise, the opposing edges of first and second strips 24 and 26 are joined to each other along a second seam, or pleat, 30, thereby forming an enclosed, elongated tube 12. Incidentally, while flexible strips 24 and 26 are illustrated and described herein as being two separate strips joined along their edges to form an elongated tube, such tube may be formed, if desired, as a single flattened tubular wall in which seams or pleats 28 and 30 are formed at opposite sides.

As indicated in FIGS. 2, 3 and 4, the relative thickness of flexible strips 24 and 26 is substantially less than that of trailing end 16 of tube 12. Flexible strips 24 and 26 are much more pliable than the walls of tube 12 adjacent trailing end 16, thereby allowing the lumen formed between flexible strips 24 and 26 to expand under positive fluid pressure, as shown in FIG. 3, or to contract and substantially flatten, as shown in FIG. 4.

It will be recalled that one of the objectives of the present invention is to allow blood or other fluid to be aspirated from the patient's body. During aspiration, a negative pressure is typically applied to the trailing end of the catheter. While the thickened walls of tube 12 adjacent trailing end 16 are sufficiently rigid to avoid collapse when such negative pressure is applied, flexible strips 24 and 26 are more pliable, and would simply collapse against one another when subjected to such negative pressure. Accordingly, catheter 10 further includes an elongated spacing member 32 disposed within catheter tube 12. Spacing member 32 has a first end 34 extending proximate leading end 14 of catheter 10, as well as an opposing second end 36 extending proximate and just beyond transition point 22. Preferably, second end 36 of spacing member 32 is secured to the thicker cylindrical walls forming trailing end 16 of catheter tube 12 to firmly anchor spacing member 32 thereto.

As shown in FIGS. 3 and 4, spacing member 32 may include a relatively flat back wall 38 that is secured to the inner face of flexible strip 24 along its length. Opposing front wall 40 of spacing member 32 is not flat, but instead includes a series of open channels 42, 44, and 46 formed between longitudinal ribs 51, 52, 53, and 54. Each open channel 42, 44 and 46 extends along the length of spacing member 32 generally facing second flexible strip 26. Spacing member 32 is not secured to second flexible strip 26; in this manner, spacing member 32 does not prevent tube 12 from expanding into the generally rounded shape shown in FIG. 3 when fluid is infused through catheter 10. When such infusion procedure is terminated, spacing member 32 allows flexible strips 24 and 26 to collapse toward one another into the substantially flattened configuration shown in FIG. 4. As indicated in FIG. 4, when tube 12 assumes its substantially flattened configuration, tube 12 can lay against the wall of blood vessel 48, or some other duct within the patient's body, thereby occupying a minimum cross section area of the vessel, and also presenting a minimal exposed surface area.

Referring to FIG. 4, should it be desired to aspirate fluid from blood vessel/duct 48, then negative pressure applied to trailing end 16 of catheter 10 will draw flexible strip 26 toward front wall 40 of spacing member 32. However, the open channels 42, 44 and 46 remain open and continuous in their lengthwise orientation, and allow fluid to be aspirated from leading end 14 of catheter tube 12.

It may be advantageous to incorporate a stripe of radiopaque material 50 within spacing member 32 extending therealong for allowing the position of catheter tube 12 to be more readily viewed within the patient's body by X-rays, fluoroscope, or the like. In this manner, a physician can verify that leading end 14 has been sufficiently advanced through a blood vessel or other duct during placement of catheter 10 within the patient's body.

The walls of tube 12 are preferably made from an extrudable plastic material, such as polyethylene, polyethylene teraphthalate, and/or polyvinyl chloride. Ideally, catheter tube 12, including the thicker walls adjacent trailing end 16, the thinner strips 24 and 26, and spacing member 32, are all formed from the same material as a single extrusion process. In the preferred embodiment of the present invention, the collapsible plastic strips 24 and 26 are inelastic, and during infusion, the leading end of tube 12 expands to a fixed "diameter", irrespective of the positive pressure applied to the infused fluid. If desired, however, such strips may be made of an elastic material.

Turning to FIGS. 5–8, an alternate embodiment of the present invention is shown in the form of a substantially collapsible dual lumen catheter apparatus. Dual lumen catheter 60 includes an elongated tube 62 having a leading end 64 and an opposing trailing end 66. Leading end 64 provides a pair of ports within the body, following placement of catheter 60, through which infused fluids introduced at trailing end 66 can be delivered into a patient's body. Leading end 64 of catheter 60 can also serve as a port within the body through which blood or other fluids can be withdrawn from the patient's body via trailing end 66.

As shown in FIG. 5, trailing end 66 of tube 62 is coupled to a Y-connector hub 68. A pair of connector tubes 70 and 72 extend from connector hub 68, each terminating in a luer lock connector fitting, such as 74 and 76, for communicating with first and second lumens within catheter tube 62. As indicated, a pair of clamps 78 and 80 may also be provided to selectively close off one or both lumens of catheter 60. Suture wing 82 is rotatably secured to connector hub 68 and allows for catheter 60 to be sutured to the patient's skin following placement to help prevent catheter 60 from becoming inadvertently dislodged.

As shown in FIG. 6, the trailing end 66 of catheter tube 62 has a substantially circular cross-section and is of substantial thickness for allowing tube 62 to maintain its circular shape even when trailing end 66 extends through a puncture tract formed in skin, blood vessel walls, or other tissues of the patient's body. While trailing end 66 of catheter tube 62 is flexible, it is still sufficiently rigid to avoid collapse or buckling along the puncture tract, and to prevent damage to tube 62 arising from long term manipulation of catheter 60 following placement. As shown in FIG. 5, trailing end 66 extends from connector hub 68 to a transition point designated by reference numeral 84. Visible within FIG. 6 is spacing member 86, which will be described in greater detail below. As shown in FIG. 6, spacing member 86 divides catheter tube 62 into a first lumen 88 and a second lumen 90. First lumen 88 communicates with connector tube 72, and second lumen 90 communicates with connector tube 70.

Once again, the portion of catheter tube 62 which extends from leading end 64 to transition point 84 is intended to be partially collapsible in order to minimize the cross-sectional area occupied by catheter tube 62 within the patient's body. Referring to FIGS. 7 and 8, the portion of catheter tube 62 extending between leading end 64 and transition point 84 includes a first elongated, generally flattened strip 92 of a flexible material, as well as a second elongated, generally flattened strip 94 of flexible material. These first and second flexible strips 92 and 94 each have a leading end adjacent leading end 64 of tube 62, as well as opposing trailing ends adjacent transition point 84. A first edge of strip 92 and a first edge of strip 94 are joined to a corresponding first side edge of spacing member 86. Preferably, a pleat 96 is formed along strip 92 just above spacing member 86 for allowing strip 92 to fold or flatten at such point. A similar pleat 98 is formed along strip 94 just above spacing member 86 for allowing strip 94 to fold or flatten at such point.

Likewise, the opposing edges of first and second strips 92 and 94 are joined to a corresponding second side edge of spacing member 86. Preferably, a pleat 100 is formed along strip 92 just below spacing member 86 for allowing strip 92 to fold or flatten at such point. A similar pleat 102 is formed along strip 94 just below spacing member 86 for allowing strip 94 to fold or flatten at such point. Incidentally, while flexible 92 and 94 are illustrated and described herein as being two separate strips joined along their edges to spacing member 86, such strips may be formed, if desired, as a single tubular wall secured at opposing points to the opposing sides of spacing member 86, and having pleats 96, 98, 100 and 102 formed therein.

As indicated in FIGS. 6, 7 and 8, the relative thickness of flexible strips 92 and 94 is substantially less than that of trailing end 66 of catheter tube 62. Flexible strips 92 and 94 are much more pliable than the walls of tube 62 adjacent trailing end 66, thereby allowing the lumens formed between each of flexible strips 92 and 94 and spacing member 86 to expand under positive fluid pressure, as shown in FIG. 7, or to contract and substantially flatten, as shown in FIG. 8.

Spacing member 86 extends fully between leading end 64 and trailing end 66 of catheter 60, in order to continuously divide lumens 88 and 90 from each other. If desired, spacing member 86 can be extruded integrally with the cylindrical walls of trailing end 66 of catheter tube 62, and integrally with the thinner walls formed by flexible strips 92 and 94.

As shown in FIGS. 6–8, spacing member 86 may include a relatively flat back wall 104 facing strip 92 and an opposing front wall 106 facing strip 94. As in the case of spacing member 32 in FIGS. 3 and 4, front wall 106 of spacing member 86 is not flat, but instead includes a series of open channels each of which extends along the length of spacing member 86. Once again, spacing member 86 does not prevent catheter tube 62 from expanding into the generally rounded shape shown in FIG. 7 when fluid is infused through lumens 88 and 90 of catheter 60. When such infusion procedure is terminated, spacing member 86 allows flexible strips 92 and 94 to collapse toward one another into the substantially flattened configuration shown in FIG. 8.

Referring to FIG. 8, should it be desired to aspirate fluid from a blood vessel or duct into which catheter 60 is placed, then negative pressure applied to connector tube 72 of catheter 62 will draw flexible strip 94 toward front wall 106 of spacing member 86. However, the open channels extending through spacing member 86 remain open and continuous in their lengthwise orientation, and allow fluid to be aspirated through lumen 88 from leading end 64 of catheter tube 62. If desired, back wall 104 of spacer 86 may also have open channels formed therein, as indicated in dashed outline in FIG. 7 by reference numeral 104', thereby allowing lumen 90 to also serve as an aspiration lumen.

If desired, additional collapsible lumens may be provided; for example, in FIG. 11, a triple-lumen catheter 126 is illustrated in cross-section. Triple-lumen catheter 126 is similar to the dual lumen catheter 62 shown in FIG. 8, and those components and features shown in FIG. 11 which correspond to those already described above in conjunction with FIG. 8 have been designated by like reference numerals. As indicated in FIG. 11, a third strip 128 of flexible material has a first edge thereof joined to the first side edge of spacing member 86, and has a second opposing edge thereof joined to the second side edge of spacing member 86. A collapsible lumen 130 is thereby formed between strip 128 and strip 92. Preferably, a pleat 132 is formed along strip 128 just above spacing member 86 for allowing strip 128 to fold or flatten at such point. A similar pleat 134 is formed along strip 128 just below spacing member 86 for allowing strip 128 to fold or flatten at such point. Catheter 126 thereby provides three lumens, 88, 90, and 130, each of which communicates with a separate connecting tube at the trailing end of the catheter for allowing separate fluids to be infused independently through all three lumens.

FIGS. 9 and 10 illustrate a further embodiment of a single-lumen catheter, designated generally by reference numeral 110, embodying the teachings of the present invention. Within FIGS. 9 and 10, only that portion of catheter 110 adjacent the leading end of such catheter, and designed to lie within the patient's body, is illustrated in cross-section, it being understood that such catheter includes a more rigid, cylindrical trailing end and connector hub like that shown in FIG. 1.

FIG. 10 shows the configuration of catheter 110 when in its collapsed state, i.e., when no infusion operation is being performed. As can be seen in FIG. 10, the semi-collapsible portion of catheter 110 includes a crescent-shaped reinforcement wall 112. As indicated in FIG. 10, reinforcement wall 112 is thickest in its middle region 114, gradually tapers upwardly toward an upper end region 116 of reduced thickness, and gradually tapers downwardly toward a lower end region 118 of reduced thickness. The thickness of middle region 114 approximates the thickness of the more rigid walls of catheter 110 adjacent the connector hub (not shown). In contrast, the thickness of upper end region 116 and lower end region 118 approaches that of collapsible flexible strips 24 and 26 in FIG. 3. Thus, upper end region 116 and lower end region 118 are less resistant to deformation due to pressures exerted thereupon.

As further indicated in FIGS. 9 and 10, a flexible strip of material 120 has its upper and lower edges joined with the edges of upper end region 116 and lower end region 118 of reinforcement wall 112, thereby sealing off the interior of reinforcement wall 112, and forming a lumen 122 therein. Strip 120 is of a thickness similar to that of strips 24 and 26 in FIG. 2, and hence, strip 120 is entirely deformable and collapsible relative to lateral deformation. Strip 120 is, however, inelastic, and resists stretching. Preferably, reinforcing wall 112 and strip 120 are extruded together from the same material as a single extrusion for manufacturing ease. Reinforcing wall 112 is bowed outwardly at end regions 116 and 118, and creates just enough tension or springiness to draw strip 120 taut, much like the string on a hunting bow, when no infusion procedure is being performed.

However, when lumen 122 is used to infuse fluid into a blood vessel, the pressure within lumen 122 is sufficient to overcome the tension of reinforcing wall 122, allowing strip 120 to expand outwardly away from reinforcing wall 112. The forces exerted by strip 120 on upper end region 116 and lower end region 118 of reinforcing wall 112 cause reinforcing wall to flatten somewhat and become more rounded, thereby allowing catheter 110 to assume the generally rounded shape shown in FIG. 9 during infusion.

Referring to FIG. 10, if it is necessary to aspirate fluid from the blood vessel or other body duct, and if the negative pressure to be applied to catheter 110 is not too great, then tension of reinforcing wall 112 may be sufficient to maintain lumen 122 open without the aid of any spacing members. On the other hand, a wire 124 may be secured along the interior of middle region 114 of reinforcing wall 112 in order to help assure that strip 120 does not seal off entirely against reinforcing wall 112. In lieu of a wire, element 124 could simply be one or more cylindrical, longitudinally-extending ribs co-extruded with reinforcing wall 112.

In order to use catheters 10, 60, and 110 of the type described above, such catheters must first be placed within the body, as within a vein, for example. Two such placement procedures will now be described. In the first placement procedure, an introducer sheath is used to facilitate placement of the catheter. An entry path is established through the skin and into the blood vessel. Such an entry path may be established, by way of example, using the Seldinger technique by initially inserting a hollow needle into the vein, threading a guide wire through the needle and into the vein, and then withdrawing the needle while leaving the guide wire in place. The leading end of a conventional peel-away (or "pull-apart") introducer sheath, loaded over a stiffening dilator, is threaded over the guide wire and guided into the vein. Once the leading end of the introducer sheath is placed in the vein, the dilator and guide wire can be withdrawn.

The leading end of catheter 10, 60, or 110 may then be inserted through the trailing end of the introducer sheath and advanced into the vein. Spacing members 32 and 86, and reinforcing wall 112, are sufficiently rigid along their length to prevent catheter tubes 12 and 62, and lumen 122, respectively, from buckling during such placement procedure. Proper placement of the leading end 14 of the catheter can be confirmed using X-rays, fluoroscopy, or ultrasound. Once proper placement of the leading end 14 of catheter 10 is confirmed, the introducer sheath is removed by pulling apart the opposing sides thereof, and peeling it away, leaving only the catheter within the vein.

A second placement method omits the introducer sheath and instead requires the physician to guide the catheter over a guide wire. For example, in the case of catheter 10, the physician first places a guide wire into the vein in the manner described above; the guide wire preferably is sized to occupy as much space within catheter tube 12 as possible, thereby providing support for collapsible strips 24 and 26. The physician then threads leading end 14 of catheter 10 over the exposed trailing end of the guide wire and slides catheter 10 along the guide wire until leading end 14 is proximate the skin entry site. Catheter 10 is further advanced, forcing leading end 14 of catheter 10 through the skin entry site and into the vein until leading end 14 is positioned at the desired location within the vein. At such time, the guide wire can be withdrawn, leaving catheter 10 in place.

If desired, the two aforementioned placement techniques can be combined; for example, the guide wire can be left in place after inserting the introducer sheath, and the catheter can then be threaded over the trailing end of the guide wire and advanced through the introducer sheath and into the vein, after which both the guide wire and the introducer sheath are removed. Alternatively, once the introducer sheath is placed, the first guide wire used to place the introducer sheath can be removed; the catheter can then be pre-loaded over a second guide wire to help support the collapsible wall portions of the catheter, and the catheter and second guide wire are then advanced as a unit through the introducer sheath until the catheter is positioned in a desired location within the vein, at which time both the guide wire and the introducer sheath can be removed.

Those skilled in the art will now appreciate that an improved, partially collapsible catheter has been described which presents minimal obstruction to blood flow within a vein, which presents minimal surface area in contact with blood flowing in the vein, but which nonetheless permits fluids to be aspirated from the patient's body. Though the disclosed catheter occupies a minimal cross-section when no fluids are being infused, and thereby reduces the likelihood of clots forming in the blood vessel, it nonetheless provide a significant fluid flow path into the body during infusion.

While the present invention has been described with respect to several preferred embodiments thereof, such description is for illustrative purposes only, and is not to be construed as limiting the scope of the invention. For example, while the detailed description of the preferred embodiments of the present invention have been directed to conventional catheters having connector hubs adapted to remain outside the patient's body, those skilled in the art will appreciate that catheter tubes of the type described and claimed herein may also be provided in the form of an implantable blood access port device that lies entirely below the patient's skin, and which is accessed by needles or the like; for purposes of the present application, the term "catheter" is intended to include such implantable blood access ports. Various modifications and changes may be made to the described embodiments by those skilled in the art without departing from the true spirit and scope of the invention as defined by the appended claims.

I claim:

1. A substantially collapsible catheter apparatus for providing a passage into a patient's body to infuse fluids therein and/or to aspirate fluids therefrom, said catheter comprising in combination:

a. a catheter tube having a longitudinal axis, said catheter tube having leading and trailing ends and including:
   i. a reinforcing wall forming a portion of said catheter tube, said reinforcing wall extending between the leading and trailing ends of said catheter tube and having opposing first and second side edges; and
   ii. a flexible strip of material extending along a predetermined length from the leading end of said catheter tube to a point generally proximate the trailing end of said catheter tube and having first and second opposing edges, the first edge of said strip being joined along the first side edge of said reinforcing wall, and the second edge of said strip being joined along the second side edge of said reinforcing wall, wherein said reinforcing wall and said strip enclose a lumen therebetween, said strip being collapsible and non-resistant to lateral deformation;

b. the trailing end of said catheter tube being adapted to receive fluid to be infused into, and to convey fluid aspirated from, a patient's body;

c. the leading end of said catheter tube providing a port through which infused fluid received at the trailing end of said catheter tube can be introduced into a patient's body, and through which aspirated fluid can be removed from a patient's body;

d. said strip expanding away from said reinforcing wall to a generally rounded shape when fluid is infused through said catheter tube into a patient, and said strip being deformable toward said reinforcing wall to a more flattened configuration when infusion is terminated; and e. said reinforcing wall of said catheter tube including preventing means secured to said reinforcing wall and extending substantially along said predetermined length of said flexible strip of material from the leading end of said catheter tube to a point generally proximate the trailing end of said catheter tube for preventing said strip from entirely sealing said lumen during aspiration of fluid through said lumen.

2. The apparatus recited by claim 1 wherein said preventing means includes at least one rib extending from said reinforcing wall for spacing said strip from said reinforcing wall.

3. The apparatus recited by claim 1 wherein said preventing means includes at least one channel formed longitudinally within said reinforcing wall.

4. The apparatus recited by claim 1 wherein said opposing first and second side edges of said reinforcing wall are bowed outward to stretch said strip, and wherein said preventing means comprises said outwardly bowed opposing side edges of said reinforcing wall.

5. A substantially collapsible catheter apparatus recited by claim 1 wherein said reinforcing wall is flexible but resists collapse along the longitudinal axis of said catheter tube.

6. A substantially collapsible catheter apparatus for providing a passage into a patient's body to infuse fluids therein and/or to aspirate fluids therefrom, said catheter comprising in combination:
   a. a first elongated, generally flattened strip of flexible material having leading and trailing ends and having first and second opposing edges;
   b. a second elongated, generally flattened strip of flexible material having leading and trailing opposing ends and having first and second opposing edges, the first edge of said second strip being joined with the first edge of said first strip, and the second edge of said first strip being joined with the second edge of said second strip to form an elongated tube having opposing leading and trailing ends;
   c. an elongated spacing member disposed within said elongated tube formed by said first and second strips of flexible material, said spacing member having a leading end extending proximate the leading ends of said first and second strips of flexible material, and said spacing member having a trailing end extending proximate the trailing ends of said first and second strips of flexible material, said spacing member being secured to said first strip of flexible material but not to said second strip of flexible material, said spacing member having at least one open channel extending therealong and facing said second strip of flexible material, said spacing member allowing said first and second strips of flexible material to collapse toward one another into a substantially flattened configuration in the absence of infusion fluid while maintaining a channel to aspirate fluid from the patient's body;
   d. the trailing end of said tube being adapted to receive fluid to be infused into, and to convey fluid aspirated from, a patient's body;
   e. the leading end of said tube providing a port through which infused fluid received at the trailing end of said tube can be introduced into a patient's body, and through which aspirated fluid can be removed from a patient's body;
   f. said tube expanding to a generally rounded shape when fluid is infused therethrough into a patient, and collapsing back, to a substantially flattened configuration when infusion is terminated.

7. The apparatus recited by claim 6 including a radiopaque material extending therealong for allowing the position of the tube to be viewed within the patient's body by X-rays, fluoroscope, or the like.

8. The apparatus recited by claim 6 wherein the trailing end of said tube includes a catheter hub, the trailing end of said tube further including a skin entry portion extending from said hub for passing through the patient's skin and being relatively rigid for preventing damage to said tube arising from long term manipulation of said catheter following placement.

9. The apparatus recited by claim 6 wherein said first and second elongated, generally flattened strips of flexible material are made of plastic.

10. The apparatus recited by claim 9 wherein said plastic is selected from the group of plastics consisting of polyethylene, polyethylene teraphthalate, and polyvinyl chloride.

11. The apparatus recited by claim 9 wherein said plastic is inelastic.

12. A substantially collapsible dual lumen catheter apparatus for providing passages into a patient's body to infuse fluids therein and/or to aspirate fluids therefrom, said dual lumen catheter comprising in combination:
   a. a first elongated, generally flattened strip of flexible material having leading and trailing opposing ends and having first and second opposing edges;
   b. a second elongated, generally flattened strip of flexible material having leading and trailing opposing ends and having first and second opposing edges, the first edge of said second strip being joined with the first edge of said first strip, and the second edge of said first strip being joined with the second edge of said second strip to form an elongated tube having a trailing end proximate the trailing ends of said first and second flattened strips of flexible material;
   c. an elongated spacing member disposed within said elongated tube formed by said first and second strips of flexible material, said spacing member having a leading end extending proximate the leading end of at least one of said first and second strips of flexible material, and said spacing member having a trailing end extending proximate the trailing ends of said first and second strips of flexible material, said spacing member having first and second opposing side edges, the first side edge of said spacing member being joined with the first edges of said first and second strips of flexible material, and the second side edge of said spacing member being joined with the second edges of said first and second strips of flexible material, said spacing member dividing said elongated tube into first and second lumens, said spacing member having at least one open channel extending therealong and facing said first strip of flexible material within the first lumen, said spacing member allowing said first strip of flexible material to collapse toward said spacing member into a substantially flattened configuration in the absence of infusion fluid within the first lumen, said spacing member allowing said second strip of flexible material to collapse toward said spacing member into a substantially flattened configuration in the absence of infusion fluid within the second lumen, said spacing member maintaining a channel within the first lumen to aspirate fluid from the patient's body through the first lumen;
   d. first and second connector tubes, said first connector tube being coupled to the first lumen proximate the trailing end of said elongated tube, said first connector tube being adapted to supply fluid to the first lumen during an infusion operation and to remove fluid from the first lumen during an aspiration operation, said second connector tube being coupled to the second lumen proximate the trailing end of said elongated tube and adapted to supply fluid to the second lumen for infusion into a patient's body;

e. the leading end of said first flattened strip of flexible material providing a first port communicating with the first lumen through which infused fluid received at the trailing end of said elongated tube via the first connector tube can be introduced into a patient's body, said first port also permitting fluid to be aspirated from a patient's body through the first lumen and first connector tube, and the leading end of said second flattened strip of flexible material providing a second port communicating with the second lumen through which infused fluid received at the trailing end of said elongated tube via said second connector tube can be infused into a patient's body;

f. said elongated tube expanding to a generally rounded shape when fluid is infused through either of the first or second lumens into a patient's body, said elongated tube collapsing back to a substantially flattened configuration when neither the first nor second lumen is being used to infuse fluid into the patient's body.

13. The apparatus recited by claim 12 including a radiopaque material extending therealong for allowing the position of the elongated tube to be viewed within the patient's body by X-rays, fluoroscope, or the like.

14. The apparatus recited by claim 12 wherein the trailing end of said elongated tube is coupled by a skin entry portion to a catheter hub, said skin entry portion extending from the trailing end of said elongated tube to said hub for passing through the patient's skin and being relatively rigid for preventing damage to said elongated tube arising from long term manipulation of said catheter following placement.

15. The apparatus recited by claim 12 wherein said first and second elongated, generally flattened strips of flexible material are made of plastic.

16. The apparatus recited by claim 15 wherein said plastic is selected from the group of plastics consisting of polyethylene, polyethylene teraphthalate, and polyvinyl chloride.

17. The apparatus recited by claim 15 wherein said plastic is inelastic.

18. The apparatus recited by claim 12 including a third elongated, generally flattened strip of flexible material having leading and trailing opposing ends and having first and second opposing edges, the first edge of said third strip being joined with the first edges of said first and second strips, and the second edge of said third strip being joined with the second edges of said first and second strips to form a third collapsible fluid conducting lumen.

19. A substantially collapsible catheter apparatus for providing a passage into a patient's body to infuse fluids therein and/or to aspirate fluids therefrom, said catheter comprising in combination:

a. a catheter tube, said catheter tube having leading and trailing ends and including:

i. a reinforcing wall forming a portion of said catheter tube, said reinforcing wall extending from the leading end of said catheter tube to a point generally proximate the trailing end of said catheter tube and having, in cross-section, a generally crescent-shaped configuration including a relatively thick middle region resistant to deformation, and tapering toward a pair of relatively thin end regions that are not as resistant to deformation; and ii. a flexible strip of material extending from the leading end of said catheter tube to a point generally proximate the trailing end of said catheter tube and having first and second opposing edges, the first edge of said strip being joined along one end region of said reinforcing wall, and the second edge of said strip being joined along a second end region of said reinforcing wall, wherein said reinforcing wall and said strip enclose a lumen therebetween, said strip being collapsible and non-resistant to lateral deformation;

b. the trailing end of said catheter tube being adapted to receive fluid to be infused into, and to convey fluid aspirated from, a patient's body;

c. the leading end of said catheter tube providing a port through which infused fluid received at the trailing end of said catheter tube can be introduced into a patient's body, and through which aspirated fluid can be removed from a patient's body;

d. said reinforcing wall being bowed outwardly to bias the end regions thereof apart from one another and thereby stretch said strip into a flattened configuration between its opposing edges when no fluid is being infused through said catheter tube;

e. said strip expanding to a generally rounded shape when fluid is infused through said catheter tube into a patient, and said strip returning to said flattened configuration when infusion is terminated.

20. The apparatus recited by claim 19 including a radiopaque material extending along said catheter tube for allowing the position of said catheter tube to be viewed within the patient's body by X-rays, fluoroscope, or the like.

21. The apparatus recited by claim 19 wherein the trailing end of said catheter tube includes a catheter hub, the trailing end of said catheter tube further including a skin entry portion extending from said hub for passing through the patient's skin and being relatively rigid for preventing damage to said tube arising from long term manipulation of said catheter following placement.

22. The apparatus recited by claim 19 wherein said reinforcing wall and strip of flexible material are made of plastic.

23. The apparatus recited by claim 22 wherein said plastic is selected from the group of plastics consisting of polyethylene, polyethylene teraphthalate, and polyvinyl chloride.

24. The apparatus recited by claim 22 wherein said plastic is inelastic.

25. The apparatus recited by claim 19 including a spacing member secured to the interior of said reinforcing wall and extending therealong for preventing said strip from flattening entirely against said reinforcing wall when fluid is aspirated from said catheter tube.

* * * * *